(12) United States Patent
Tian et al.

(10) Patent No.: US 11,965,734 B2
(45) Date of Patent: Apr. 23, 2024

(54) METHOD AND SYSTEM FOR QUANTITATIVELY EVALUATING SURFACE ROUGHNESS OF ORGANIC PORE OF KEROGEN IN SHALE

(71) Applicant: Northeast Petroleum University, Heilongjiang (CN)

(72) Inventors: Shansi Tian, Heilongjiang (CN); Bo Liu, Heilongjiang (CN); Xiaofei Fu, Heilongjiang (CN); Fang Zeng, Heilongjiang (CN); Xu Dong, Heilongjiang (CN); Yifei Gao, Heilongjiang (CN); Zhenjie Luo, Heilongjiang (CN)

(73) Assignee: Northeast Petroleum University, Daqing (CN)

( * ) Notice: Subject to any disclaimer, the term of this patent is extended or adjusted under 35 U.S.C. 154(b) by 841 days.

(21) Appl. No.: 17/061,550

(22) Filed: Oct. 1, 2020

(65) Prior Publication Data
US 2022/0057199 A1 Feb. 24, 2022

(30) Foreign Application Priority Data
Aug. 24, 2020 (CN) .......................... 202010856007.9

(51) Int. Cl.
*G01B 11/30* (2006.01)
*E21B 49/02* (2006.01)
(Continued)

(52) U.S. Cl.
CPC .............. *G01B 11/30* (2013.01); *E21B 49/02* (2013.01); *G01B 9/02085* (2013.01); *G01N 1/04* (2013.01);
(Continued)

(58) Field of Classification Search
CPC ................................ G01B 11/30; E21B 49/02
See application file for complete search history.

(56) References Cited

U.S. PATENT DOCUMENTS 10,830,027 B2 * 11/2020 Hull ........................ E21B 49/02
11,150,206 B2 * 10/2021 Eichmann .............. G01Q 60/42
(Continued)

FOREIGN PATENT DOCUMENTS

CN 102346130 A * 2/2012
CN 103499322 A * 1/2014
(Continued)

*Primary Examiner* — Ryan D Walsh
(74) *Attorney, Agent, or Firm* — Mark C. Johnson; Johnson Dalal (57) ABSTRACT

The present invention relates to a method and system for quantitatively evaluating surface roughness of an organic pore of kerogen in shale. The method includes: making a shale sample; applying a circle of silver-painted conductive tape on the edge of the shale sample to obtain a processed sample; conducting image scanning on the processed sample to obtain a scanned image; determining a kerogen area according to the scanned image; determining an organic pore area according to the kerogen area; carrying out gridding treatment on the organic pore area to obtain multiple grid cells; adopting double integral calculation on each of the grid cells to obtain the areas of the multiple grid cells; summing each of the areas to obtain the surface area of the organic pore; and evaluating surface roughness of the organic pore according to the surface area of the pore.

5 Claims, 4 Drawing Sheets

(51) Int. Cl.
    *G01B 9/02*     (2022.01)
    *G01N 1/04*     (2006.01)
    *G01N 1/28*     (2006.01)
    *G01N 1/32*     (2006.01)
    *G01N 1/36*     (2006.01)
    *G01N 15/08*     (2006.01)
    *G01N 33/24*     (2006.01)
    *G01Q 60/24*     (2010.01)

(52) U.S. Cl.
    CPC ............... *G01N 1/286* (2013.01); *G01N 1/32* (2013.01); *G01N 1/36* (2013.01); *G01N 15/088* (2013.01); *G01N 33/24* (2013.01); *G01N 33/241* (2013.01); *G01Q 60/24* (2013.01); *G01B 2210/52* (2013.01)

(56) References Cited

U.S. PATENT DOCUMENTS

| | | | |
|---|---|---|---|
| 11,268,919 B2 * | 3/2022 | Eichmann | ............ G01N 33/241 |
| 2014/0048694 A1 * | 2/2014 | Pomerantz | ........... G01N 33/241 |
| | | | 250/255 |

FOREIGN PATENT DOCUMENTS

| | | | | |
|---|---|---|---|---|
| CN | 108519264 A | * | 9/2018 | ............. G01N 1/286 |
| CN | 110146533 A | * | 8/2019 | ............. G01N 15/08 |
| CN | 111366753 A | * | 7/2020 | |

* cited by examiner

METHOD AND SYSTEM FOR QUANTITATIVELY EVALUATING SURFACE ROUGHNESS OF ORGANIC PORE OF KEROGEN IN SHALE

TECHNICAL FIELD

The present invention relates to the field of evaluating kerogen parameters in shale, and in particular to a method and system for quantitatively evaluating surface roughness of an organic pore of kerogen in shale.

BACKGROUND

Shale oil refers to oil accumulation that is occurred in shale formation which is rich in organic matters and mainly of a nanoscale pore size. Shale is not only a hydrocarbon source rock but also a reservoir rock, which is a typical self-generating and self-storing oil accumulation. Shale oil has the characteristics of continuous distribution, self-generation and self-storage, huge resources and so on. It may become an important substitute energy for oil and gas in China in the future, which is of great significance for alleviating energy crisis and promoting sustainable economic development. According to EIA data in 2016, the recoverable quantity by the shale oil technology in the world is 345 billion barrels, China ranks third in the world with a resource quantity of 32 billion barrels. In recent years, China has attached great importance to the shale oil resource and explored it, and has achieved a certain degree of success. For example, Sinopec obtained industrial oil run in shale formations of Anshen 1 well and Biye HF1 well in Biyang sag, and PetroChina also obtained industrial oil run in shale formations of Shugu 165 well in Liaohe Oilfield and Pushen 18-1 well in Puyang Depression. However, China's lacustrine shale has developed a multi-scale pore-fracture system, which is characterized by various pore types, nano-scale pore development, complex material composition and strong heterogeneity. As a result, the shale oil has poor fluidity, the existing shale oil wells have low output and rapid decline in output, and thus exploration and development of the shale oil still have a long way to go. The microscopic characteristics of shale reservoir pores and the occurrence and mobility of the shale oil are of great significance for evaluating the resource potential of the shale oil and predicting favorable areas. Shale reservoir characteristics are namely the size and distribution of pores, throats and fractures of the shale, the composition characteristics of minerals and organic matters, and the reservoir space characteristics of different material compositions. The shale reservoir characteristics are closely related to the occurrence state and mobility of the shale oil, so the shale reservoir characteristics are the primary problem to be solved in geological research of shale oil.

Scholars at home and abroad have done a lot of researches on the pores and pore throat structure of the shale at a post-mature stage, and have known more about the microstructure and gas-bearing property of the shale at a gas-forming stage. However, the research on pore microscopic characteristics of a shale reservoir dominated by oil formation in an oil window stage is less until this project is established, especially the quantitative evaluation of pores that are developed as controlled by different minerals is lacking, and the knowledge about the evolution mechanism of pores during shale evolution was less. Moreover, the specific surface area and adsorption capacity per unit area of the shale determine the adsorption capacity of the shale for shale oil. However, for the researches on the specific surface area of the shale, the previous studies are mostly focused on the influence of pore size distribution on the specific surface area, but there is no good research on another key parameter for controlling the specific surface area, i.e., the roughness.

SUMMARY

An objective of the present invention is to provide a method and system for quantitatively evaluating surface roughness of an organic pore of kerogen in shale, which can improve the accuracy in evaluation of the surface roughness of an organic pore of kerogen in shale.

To achieve the above purpose, the present invention provides the following technical solutions.

A method for quantitatively evaluating surface roughness of an organic pore of kerogen in shale includes:
  making a shale sample;
  applying a circle of silver-painted conductive tape on the edge of the shale sample to obtain a processed sample;
  conducting image scanning on the processed sample to obtain a scanned image;
  determining a kerogen area according to the scanned image;
  determining an organic pore area according to the kerogen area;
  carrying out gridding treatment on the organic pore area to obtain multiple grid cells;
  adopting double integral calculation on each of the grid cells to obtain the areas of the multiple grid cells;
  summing each of the areas to obtain the surface area of the organic pore; and
  evaluating surface roughness of the organic pore according to the surface area of the pore.

Optionally, the making a shale sample specifically includes:
  using a diamond wire cutting machine to obtain a standard shale core column;
  making a sheet with a set thickness according to the standard shale core column;
  mechanically polishing the sheet with a carborundum suspension to obtain a mechanically-polished sheet;
  drilling the polished sheet to obtain a cylindrical sheet sample; and
  performing argon ion beam polishing on the cylindrical sheet sample to obtain shale sample subjected to argon ion beam polishing.

Optionally, the conducting image scanning on the processed sample to obtain a scanned image specifically includes:
  conducting large-area overlap-scanning on the processed sample to obtain a scanned image.

Optionally, the determining a kerogen area according to the scanned image specifically includes:
  determining an approximate area of kerogen according to the scanned image;
  searching for three recognizable pyrite areas around the approximate area of kerogen;
  determining the three pyrite areas by a reflection light microscope of an atomic force microscope; and
  determining a middle kerogen area according to each of the pyrite areas.

Optionally, the carrying out gridding treatment on the organic pore area to obtain multiple grid cells specifically includes:
  carrying out triangle gridding treatment on the organic pore area to obtain multiple triangle grid cells.

A system for quantitatively evaluating surface roughness of an organic pore of kerogen in shale includes:
  a sample making module for making a shale sample;
  an application module for applying a circle of silver-painted conductive tape on the edge of the shale sample to obtain a processed sample;
  an image scanning module for conducting image scanning on the processed sample to obtain a scanned image;
  a kerogen area determining module for determining a kerogen area according to the scanned image;
  an organic pore area determining module for determining an organic pore area according to the kerogen area;
  a gridding treatment module for carrying out gridding treatment on the organic pore area to obtain multiple grid cells;
  an integration module for adopting double integral calculation on each of the grid cells to obtain the areas of the multiple grid cells;
  a summing module for summing each of the areas to obtain the surface area of the organic pore; and
  an evaluation module for evaluating surface roughness of the organic pore according to the surface area of the pore.

Optionally, the sample making module specifically includes:
  a cutting unit for cutting with a diamond wire cutting machine to obtain a standard shale core column;
  a sheet making unit for making a sheet with a set thickness according to the standard shale core column;
  a mechanical polishing unit for mechanically polishing the sheet with a carborundum suspension to obtain a mechanically-polished sheet;
  a drilling unit for drilling the polished sheet to obtain a cylindrical sheet sample; and
  an argon ion beam polishing unit for performing argon ion beam polishing on the cylindrical sheet sample to obtain shale sample subjected to argon ion beam polishing.

Optionally, the image scanning module specifically includes:
  an image scanning unit for conducting large-area overlap-scanning on the processed sample to obtain a scanned image.

Optionally, the kerogen area determining module specifically includes:
  a kerogen approximate area determining unit for determining an approximate area of kerogen according to the scanned image;
  a pyrite area searching unit for searching for three recognizable pyrite areas around the approximate area of kerogen;
  a pyrite area determining unit for determining the three pyrite areas by a reflection light microscope of an atomic force microscope; and
  a middle kerogen area determining unit for determining a middle kerogen area according to each of the pyrite areas.

Optionally, the gridding treatment module specifically includes:
  a gridding treatment unit for carrying out triangle gridding treatment on the organic pore area to obtain multiple triangle grid cells.

According to specific examples provided by the present invention, the present invention discloses the following technical effects.

The present invention relates a method and system for quantitatively evaluating surface roughness of an organic pore of kerogen in shale. The method includes making a shale sample; applying a circle of silver-painted conductive tape on the edge of the shale sample to obtain a processed sample; conducting image scanning on the processed sample to obtain a scanned image; determining a kerogen area according to the scanned image; determining an organic pore area according to the kerogen area; carrying out gridding treatment on the organic pore area to obtain multiple grid cells; adopting double integral calculation on each of the grid cells to obtain the areas of the multiple grid cells; summing each of the areas to obtain the surface area of the organic pore; and evaluating surface roughness of the organic pore according to the surface area of the pore. Adopting the aforementioned method can improve the identification accuracy of the kerogen area, and further improve the accuracy in evaluation of the surface roughness of the kerogen organic pore in the shale.

BRIEF DESCRIPTION OF THE DRAWING

To describe the technical solutions in the embodiments of the present invention or in the prior art more clearly, the following briefly describes the accompanying drawings required for describing the embodiments. Apparently, the accompanying drawings in the following description show some embodiments of the present invention, and a person of ordinary skill in the art may still derive other drawings from these accompanying drawings without creative efforts.

DETAILED DESCRIPTION

The following clearly and completely describes the technical solutions in the embodiments of the present invention with reference to the accompanying drawings in the embodiments of the present invention. Apparently, the described embodiments are merely a part rather than all of the embodiments of the present invention. All other examples obtained by a person of ordinary skill in the art based on the examples of the present invention without creative efforts shall fall within the protection scope of the present invention.

To make the foregoing objective, features, and advantages of the present invention clearer and more comprehensible, the present invention is further described in detail below with reference to the accompanying drawings and specific embodiments.

Figure 1:
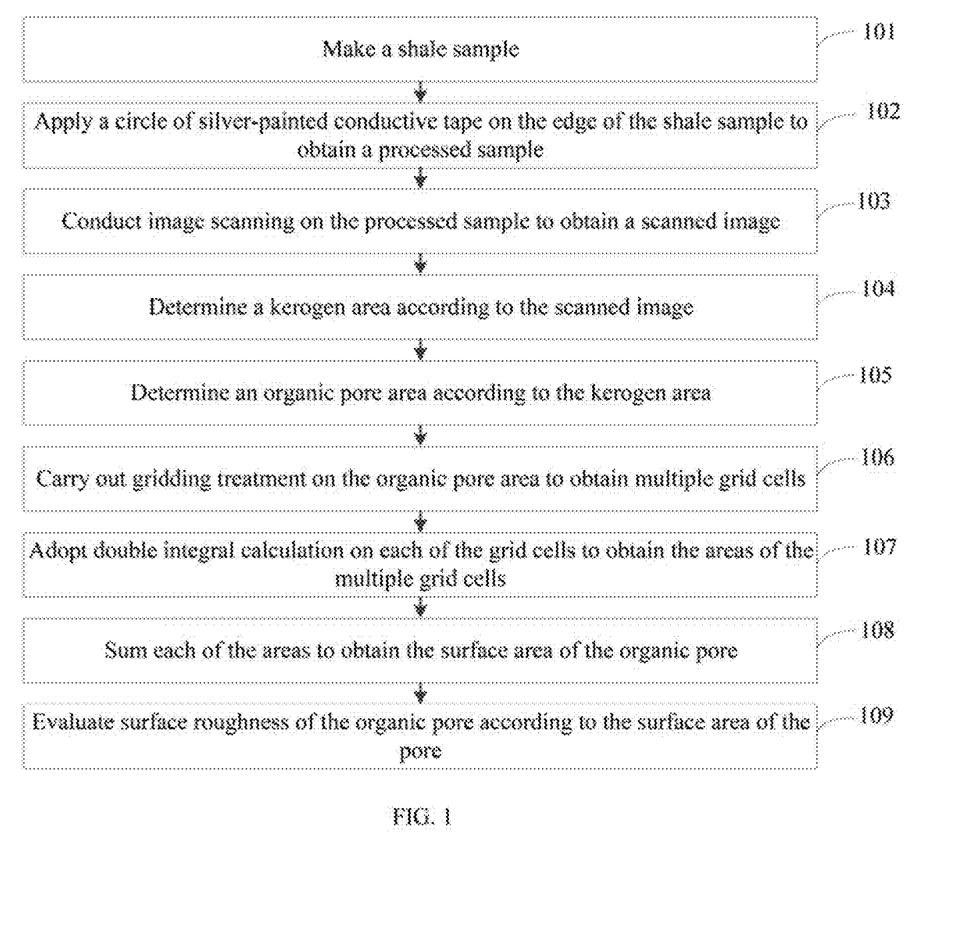
FIG. 1 is a flowchart of a method for quantitatively evaluating surface roughness of an organic pore of kerogen in shale according to the present invention.

FIG. 1 is a flowchart of a method for quantitatively evaluating surface roughness of an organic pore of kerogen in shale according to the present invention. As shown in FIG. 1, a method for quantitatively evaluating surface roughness of an organic pore of kerogen in shale includes the following steps.

Step 101: a shale sample is made, which specifically includes:
  using a diamond wire cutting machine to obtain a standard shale core column;

making a sheet with a set thickness according to the standard shale core column;

mechanically polishing the sheet with a carborundum suspension to obtain a mechanically-polished sheet;

drilling the polished sheet to obtain a cylindrical sheet sample; and performing argon ion beam polishing on the cylindrical sheet sample to obtain shale sample subjected to argon ion beam polishing.

As a preferred embodiment, in the present invention, a 2.5 cm×2.5 cm standard shale core column is obtained by using a diamond wire cutting machine. Then, a sheet with a thickness of 350 μm is made, and the sheet is mechanically polished with a 6 μm carborundum suspension for 10 minutes, with a 3 μm carborundum suspension for 10 minutes, with a 1 μm carborundum suspension for 15 minutes, and with a ¼ μm carborundum suspension for 15 minutes. After the mechanical polishing is completed, a cylindrical small sheet sample with a diameter of 3 mm is drilled on the mechanically polished sheet with an ultrasonic drilling machine available from Gatan. Finally, the sample is subjected to argon ion beam polishing with an ion beam having the energy of 5 KeV and a low ion gun angle of 15° by using an argon ion polisher available from Gatan, so that the surface of the sample is smooth enough.

Step 102: a circle of silver-painted conductive tape is applied on the edge of the shale sample to obtain a processed sample.

In order to avoid the influence of the conductive coating (gold-plated film, and carbon-plated film) on the atomic-force microscope experiment, the sample must not be coated.

Furthermore, due to the non-conductivity of the shale, in order to avoid the overexposure phenomenon of the sample under the scanning electron microscope, in this step a circle of silver-painted conductive tape is applied on the edge of the shale sample after the argon ion beam polishing.

Step 103: image scanning is conducted on the processed sample to obtain a scanned image, which specifically includes:

conducting large-area overlap-scanning on the processed sample to obtain a scanned image.

After the preparation of the sample is completed, the processed sample is subjected to image scanning with a FEI Dual Beam MK2 Helios scanning electron microscope instrument. The scanning parameters are as follows: a working distance of 4 mm, a scanning voltage of 1.5 k, a scanning current of 21 pA, a contrast ratio of 85, a brightness of 45, a scanning time of 10 μs, a contrast of 80 (slightly biased towards a backscattering mode), a resolution of 8192×8192, which makes the resultant scanning electron microscope (SEM) picture satisfies the requirements that (1) the distribution of a gray histogram should be uniform; (2) the gray probability value at the junction of the kerogen peak and the main mineral peak in the gray histogram cannot exceed 15% of the kerogen peak (it is better when the percentage is lower). The sample is subjected to large-area overlap-scanning by Aztec software available from Oxford Instruments, and finally a large-area mosaic image of 300 μm×300 μm is obtained.

Step 104: a kerogen area is determined according to the scanned image, which specifically includes:

determining an approximate area of kerogen according to the scanned image;

searching for three recognizable pyrite areas around the approximate area of kerogen;

determining the three pyrite areas by a reflection light microscope of an atomic force microscope; and determining a middle kerogen area according to each of the pyrite areas.

The sample after the electron microscope scanning experiment in the step 103 is put into a JPK NanoWizard® atomic-force microscope experimental instrument produced by JPK Instrument. Firstly, a reflection microscope self-equipped on the atomic-force microscope is utilized to find the positions of the recorded fractures and the three characteristic pyrites, so as to roughly estimate the kerogen area. Then the parameters of the atomic-force microscope instrument are adjusted. The target area is scanned preliminarily using a PeakForce™ tapping mode and utilizing a non-contact ARROW-NCR standard probe (the probe tip parameters: height: 10 μm-15 μm, a tip diameter<10 nm; parameters of a probe-tip carrying platform: length: 160 μm, width: 45 μm, thickness: 4.6 μm, a force coefficient: 42 N/m, and frequency: 285 kHz), until an area position where the profile of the kerogen area is consistent with the profile of the kerogen area under the scanning electron microscope is scanned. Finally, the found kerogen area is scanned finely by using a model EBD-AR15T high-resolution probe (the parameters of the probe-tip carrying platform: length: 125 μm, width: 30 μm, thickness: 4 μm, force coefficient: 40 N/m, and frequency: 330 kHz; the parameters of the probe tip: a height of 4 μm, a tip diameter<5 nm, and a tip inclination angle of 13°).

Figure 2:
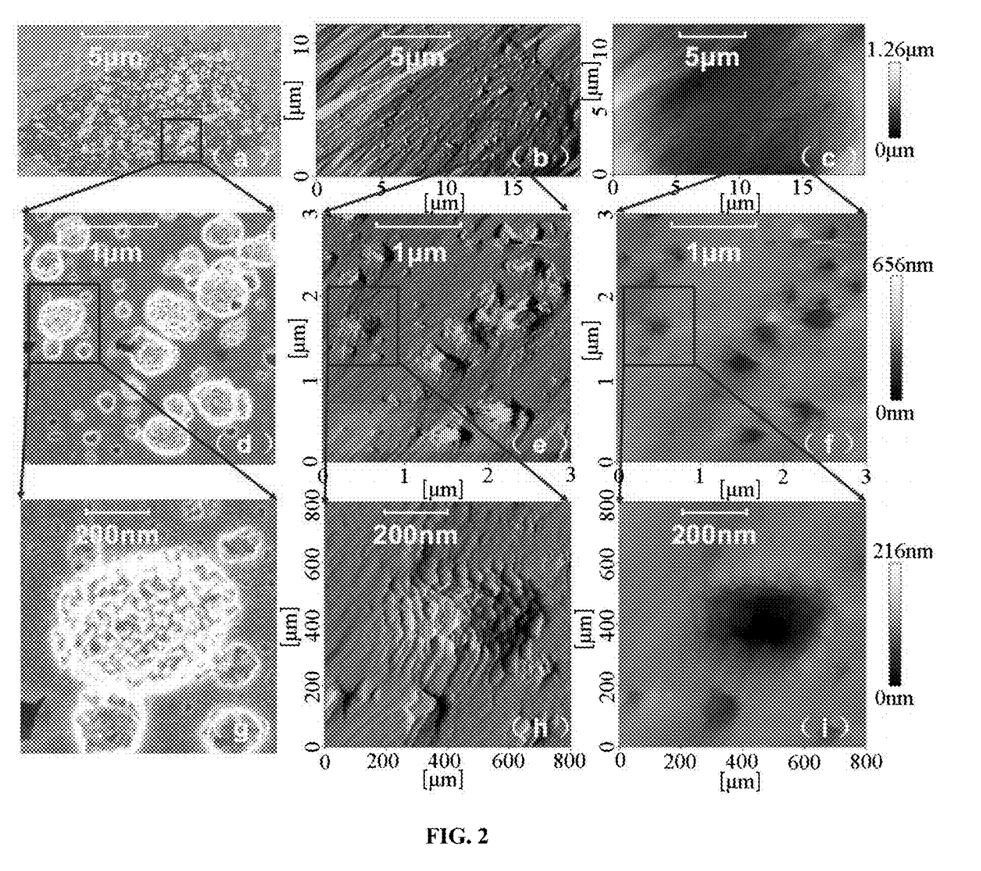
FIG. 2 is a diagram showing the characterization results of the surface roughness of a kerogen nano-scale pore of Longmaxi Formation in the well DT1, Sichuan Basin.

FIG. 2 is a diagram showing the characterization results of the surface roughness of a kerogen nano-scale pore of Longmaxi Formation in the well DT1, Sichuan Basin. In this figure, a is a SEM image of the kerogen; b is a diagram showing the AFM scanning track process of the kerogen area; c is a diagram showing the AFM surface morphology result of the kerogen area; d is a SEM image of multiple pores within the kerogen area; e is a diagram showing the AFM scanning track process of multiple pores within the kerogen area; f is a diagram showing the AFM surface morphology result of multiple pores within the kerogen area; g is a SEM image of 600 nm pores of the kerogen; h is a diagram showing the AFM scanning track process of 600 nm pores of the kerogen; and i is a diagram showing the AFM surface morphology of 600 nm pores of the kerogen. FIGS. 2a, 2d and 2g are diagrams showing the SEM results of the nano-scale pores in the kerogen area. It can be seen from the figure that the surface of the kerogen pore is not smooth, but rough and uneven, and these rough units will greatly increase the specific surface area of kerogen. However, due to the limitation of the scanning electron microscopy test, only rough units on the surface of the kerogen pore can be seen qualitatively. Therefore, after the target area is found in the scanning electron microscope experiment, we continue to quantitatively characterize the surface morphology of the kerogen pore in an AFM experiment. FIGS. 2b, 2c, 2e, 2f, 2h, and 2i are diagrams showing the scanning results of the AFM experiment, and FIGS. 2b, 2e, and 2h are diagrams showing the scanning trace process of the AFM experiment, which record the motion trajectory of the probe, but have no information such as height. FIGS. 2c, 2f, and 2i are diagrams showing the final results of surface morphology features of the pores as obtained by the AFM experiment, which record the height of each point on a surface roughness unit of the pore, and finally obtain the surface morphology features.

Step 105: an organic pore area is determined according to the kerogen area. Specifically, according to the kerogen area, amplified scanning of a local area is performed step by step to determine the organic pore area.

Step 106: gridding treatment is conducted on the organic pore area to obtain multiple grid cells, which specifically includes:

carrying out triangle gridding treatment on the organic pore area to obtain multiple triangle grid cells.

Figure 3:
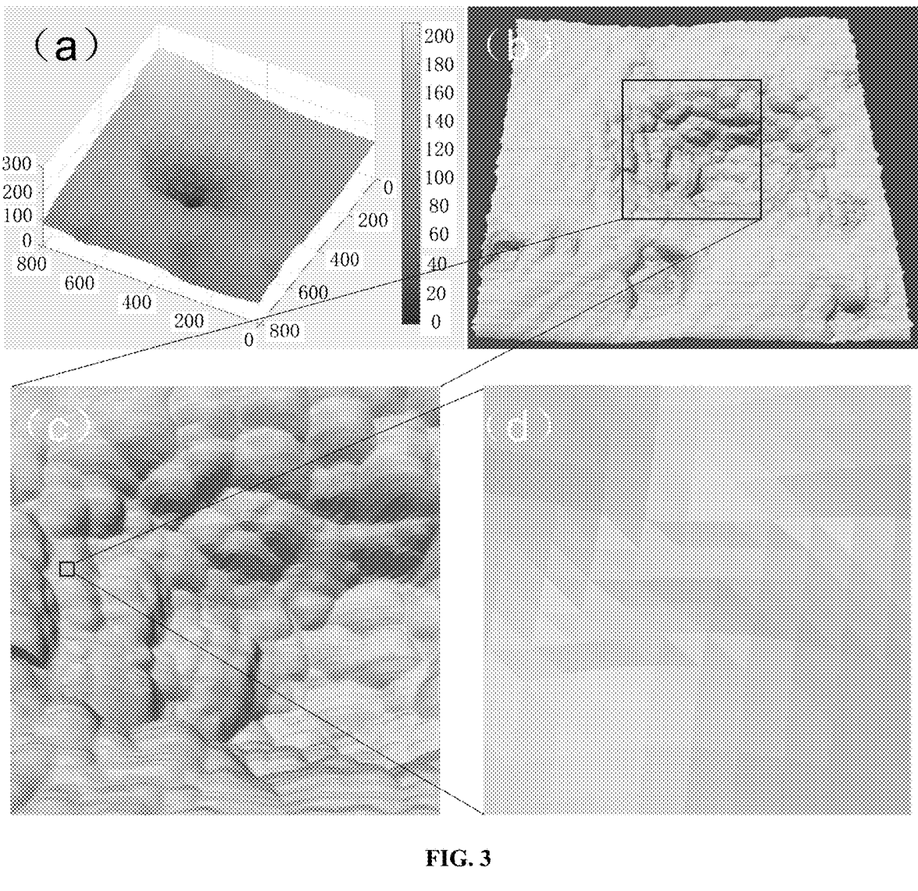
FIG. 3 is a diagram showing a process for quantitatively evaluating the surface morphology characteristics of a pore.

FIG. 3 is a diagram showing a process for quantitatively evaluating the surface morphology characteristics of a pore. In the figure, a represents a 3D map of the surface morphology of a pore; b is the triangular gridding diagram of the surface morphology features of the pore; c is a partial enlarged view of triangular gridding of the surface morphology features of the pore; and d is a partial enlarged view of triangular gridding of the surface morphology features of the pore. The scanning results of the atomic-force microscope are introduced into ParaView5.5 software, and the surface of the pore is subjected to triangular gridding by using a Triangulate module, so to divide the surface of the pore into n triangles. The surface of the pore is divided into several tiny triangle units (as shown in FIGS. 3c and 3d).

Step 107: double integral calculation is adopted on each of the grid cells to obtain the areas of the multiple grid cells.

S is set as the pore surface, f(x, y, z) is a function defined on S, and the curved face S is subjected to division T, which divides S into n small curved surfaces $S_i$ (i=1, ..., n) of which the area can be solved. The area of $S_i$ is denoted as $\Delta S_i$, the fineness of the division T is $\|T\|=\max \Delta S_i$, any point $(x_i, y_i, z_i)$ (i=1, ..., n) is taken on $S_i$, and if there is a limit, $$\lim_{\|T\|\to 0}\Sigma_k f(x_i,y_i,z_i)\Delta s_i = J \quad (1)$$

and its value has nothing to do with segmentation and point selection, then this limit J is called the first type curved surface integral of f(x, y, z) on the pore surface S, which is written as:

$$\iint_S f(x,y,z)ds = J \quad (2)$$

Then the equation of spatial pore surface S is set as z=z(x, y), (x, y)∈Ω, where Ω is the projection domain of the pore surface S on the $O_{xy}$ plane, and the function f(x, y, z) is continuous on the pore surface S. If z=z(x, y) has a continuous first-order partial derivative on Ω, then:

$$\int\int_{\Delta\sigma i}\sqrt{1+\left(\frac{\partial z}{\partial x}\right)^2+\left(\frac{\partial z}{\partial y}\right)^2} = J = \sqrt{1+\left(\frac{\partial z}{\partial x}\right)_i^2+\left(\frac{\partial z}{\partial y}\right)_i^2}\Delta\sigma i \quad (3)$$

where $\Delta\sigma_i$ is a projection domain of $\Delta S_i$ on $O_{xy}$, and $$\left(\frac{\partial z}{\partial x}\right)_i \text{ and } \left(\frac{\partial z}{\partial y}\right)_i$$

represents two partial derivatives at a certain point $(x_i, y_i)$ within $\Delta\sigma_i$. By the definition of the first type curved surface integral, the first type curved surface area is divided into the calculation of double integral:

$$\iint_s f(x, y, z)ds = \iint_{\Omega_{xy}} f(x, y, z(x, y))\sqrt{1+\left(\frac{\partial z}{\partial x}\right)^2+\left(\frac{\partial z}{\partial y}\right)^2}d\sigma \quad (4)$$

The area $\Delta S_i$ of each triangle is double integrated according to formula 4, so as to calculate its area.

Step 108: each of the areas is summed to obtain the surface area of the organic pore. Each of the areas obtained in the step 107 is cumulatively summed to obtain the final surface area of the organic pore. It can be calculated out that, for this pore with a diameter of 604.6 nm, its surface area is $6.647\times10^{-13}$ m².

Step 109: the surface roughness of the organic pore is evaluated according to the surface area of the pore.

According to formula 5 and formula 6, the surface area of the pore based on a spherical crown model is $3.467\times10^{-13}$ m², and the roughness coefficient $F_{roughness}$ of the pore surface is 1.9178. Also, the surface areas of six pores with diameters of 100 nm-300 nm near this pore are calculated. The surface areas are $4.74\times10^{-15}$ m² to $4.27\times10^{-14}$ m², and the roughness coefficients are 1.1689-1.3576. It is found through research that the surface roughness coefficient is less when the pore diameter is smaller.

Surface roughness coefficient of the pore:

$$F_{roughness}=S_{roughness}/S_{sph}=(\Sigma\Delta S_i)/(2\pi RH) \quad (5)$$

$$(R-H)^2+r^2=R^2 \quad (6)$$

where, $F_{roughness}$ refers to the surface roughness coefficient of the pore, which is dimensionless; $S_{roughness}$ is the surface area (m²) of the pore; $S_{sph}$ is the surface area (m²) of a spherical crown to be synthesized by the pore; R is the radius of the spherical crown (m); r is the pore radius (m); H is the pore height (m); and $\Delta S_i$ is the area (m²) of the i-th triangle after the triangle gridding treatment by a finite element method.

In the present invention, the pretreatment of the shale sample avoids the influence on the accuracy of the atomic-force microscope experiment, and avoids the overexposure phenomenon in the shooting process of the SEM experiment; optimization of the SEM parameters is beneficial for improving the identification accuracy of the kerogen region. Evaluating surface roughness of an organic pore of kerogen in shale by the method of the present invention is beneficial for improving the accuracy of evaluating surface roughness of an organic pore of kerogen.

Figure 4:
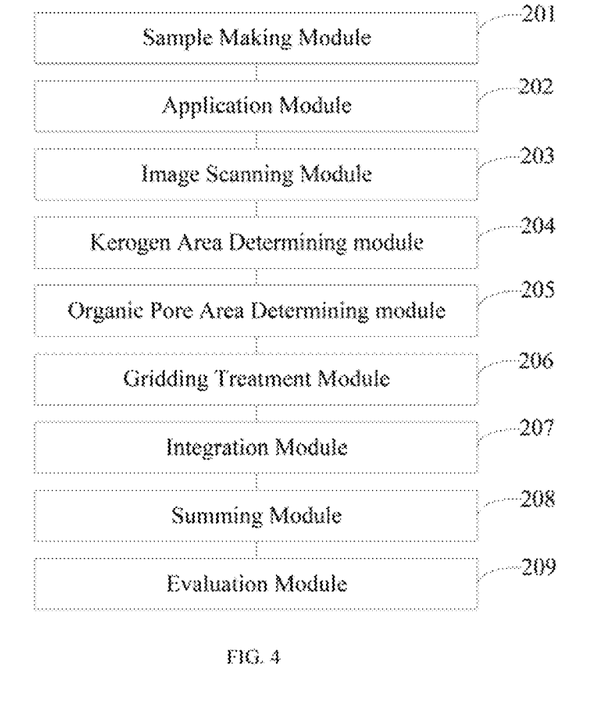
FIG. 4 is a structural diagram of a system for quantitatively evaluating surface roughness of an organic pore of kerogen in shale according to the present invention.

The present invention further provides a system for quantitatively evaluating surface roughness of an organic pore of kerogen in shale. FIG. 4 is a structural diagram of a system for quantitatively evaluating surface roughness of an organic pore of kerogen in shale according to the present invention. As shown in FIG. 4, a system for quantitatively evaluating surface roughness of an organic pore of kerogen in shale includes:

a sample making module 201 for making a shale sample;

an application module 202 for applying a circle of silver-painted conductive tape on the edge of the shale sample to obtain a processed sample;

an image scanning module 203 for conducting image scanning on the processed sample to obtain a scanned image;

a kerogen area determining module 204 for determining a kerogen area according to the scanned image;

an organic pore area determining module 205 for determining an organic pore area according to the kerogen area;

a gridding treatment module 206 for carrying out gridding treatment on the organic pore area to obtain multiple grid cells;

an integration module 207 for adopting double integral calculation on each of the grid cells to obtain the areas of the multiple grid cells;

a summing module 208 for summing each of the areas to obtain the surface area of the organic pore; and an evaluation module 209 for evaluating surface roughness of the organic pore according to the surface area of the pore.

The sample making module 201 specifically includes:
- a cutting unit for cutting with a diamond wire cutting machine to obtain a standard shale core column;
- a sheet making unit for making a sheet with a set thickness according to the standard shale core column;
- a mechanical polishing unit for mechanically polishing the sheet with a carborundum suspension to obtain a mechanically-polished sheet;
- a drilling unit for drilling the polished sheet to obtain a cylindrical sheet sample; and
- an argon ion beam polishing unit for performing argon ion beam polishing on the cylindrical sheet sample to obtain shale sample subjected to argon ion beam polishing.

The image scanning module 203 specifically includes:
an image scanning unit for conducting large-area overlap-scanning on the processed sample to obtain a scanned image.

The kerogen area determining module 204 specifically includes:
- a kerogen approximate area determining unit for determining an approximate area of kerogen according to the scanned image;
- a pyrite area searching unit for searching for three recognizable pyrite areas around the approximate area of kerogen;
- a pyrite area determining unit for determining the three pyrite areas by a reflection light microscope of an atomic force microscope; and
- a middle kerogen area determining unit for determining a middle kerogen area according to each of the pyrite areas.

The gridding treatment module 206 specifically includes:
a gridding treatment unit for carrying out triangle gridding treatment on the organic pore area to obtain multiple triangle grid cells.

Each example of the present specification is described in a progressive manner, each example focuses on the difference from other examples, and the same and similar parts between the examples may refer to each other. For a system disclosed in the examples, since it corresponds to the method disclosed in the examples, the description is relatively simple, and reference can be made to the method description.

Several examples are used for illustration of the principles and implementation methods of the present invention. The description of the embodiments is used to help illustrate the method and its core principles of the present invention. In addition, those skilled in the art can make various modifications in terms of specific embodiments and scope of application in accordance with the teachings of the present invention. In conclusion, the content of this specification shall not be construed as a limitation to the present invention.

What is claimed is:

1. A method for quantitatively evaluating surface roughness of an organic pore of kerogen in shale, comprising:
   - making a shale sample;
   - applying a circle of silver-painted conductive tape on the edge of the shale sample to obtain a processed sample;
   - conducting image scanning on the processed sample to obtain a scanned image;
   - determining a kerogen area according to the scanned image;
   - determining an organic pore area according to the kerogen area;
   - carrying out gridding treatment on the organic pore area to obtain multiple grid cells;
   - adopting double integral calculation on each of the grid cells to obtain the areas of the multiple grid cells;
   - summing each of the areas to obtain the surface area of the organic pore; and
     - evaluating surface roughness of the organic pore according to the surface area of the pore;
     - wherein the evaluating surface roughness of the organic pore according to the surface area of the pore comprises:
     - calculating a surface roughness coefficient of the pore using the following formulas $$F_{roughness} = S_{roughness}/S_{sph} = (\Sigma \Delta S_i)/(2\pi RH)$$

$$(R-H)^2 + r^2 = R^2$$

wherein, $F_{roughness}$ refers to the surface roughness coefficient of the pore, $S_{roughness}$ is the surface area of the pore, $S_{sph}$ is a surface area of a spherical crown to be synthesized by the pore, R is a radius of the spherical crown, r is a pore radius, H is a pore height, and $\Delta S_i$ is an area of an i-th triangle after the gridding treatment.

2. The method for quantitatively evaluating surface roughness of an organic pore of kerogen in shale according to claim 1, wherein the making a shale sample specifically comprises:
   - using a diamond wire cutting machine to obtain a standard shale core column;
   - making a sheet with a set thickness according to the standard shale core column;
   - mechanically polishing the sheet with a carborundum suspension to obtain a mechanically-polished sheet;
   - drilling the polished sheet to obtain a cylindrical sheet sample; and
   - performing argon ion beam polishing on the cylindrical sheet sample to obtain shale sample subjected to argon ion beam polishing.

3. The method for quantitatively evaluating surface roughness of an organic pore of kerogen in shale according to claim 1, wherein the conducting image scanning on the processed sample to obtain a scanned image specifically comprises:
   - conducting large-area overlap-scanning on the processed sample to obtain a scanned image.

4. The method for quantitatively evaluating surface roughness of an organic pore of kerogen in shale according to claim 1, wherein the determining a kerogen area according to the scanned image specifically comprises:
   - determining an approximate area of kerogen according to the scanned image;
   - searching for three recognizable pyrite areas around the approximate area of kerogen;
   - determining the three pyrite areas by a reflection light microscope of an atomic force microscope; and
   - determining a middle kerogen area according to each of the pyrite areas.

5. The method for quantitatively evaluating surface roughness of an organic pore of kerogen in shale according to claim 1, wherein the carrying out gridding treatment on the organic pore area to obtain multiple grid cells specifically comprises:
   - carrying out triangle gridding treatment on the organic pore area to obtain multiple triangle grid cells.

* * * * *